US 6,694,212 B1

(12) United States Patent
Kennedy

(10) Patent No.: US 6,694,212 B1
(45) Date of Patent: Feb. 17, 2004

(54) COMPUTER-AIDED DESIGN OF A PONTIC WITH RETAINERS

(76) Inventor: James P. Kennedy, 5509 Leatherstocking La., Stone Mountain, GA (US) 30087

( * ) Notice: Subject to any disclaimer, the term of this patent is extended or adjusted under 35 U.S.C. 154(b) by 0 days.

(21) Appl. No.: 10/107,654

(22) Filed: Mar. 27, 2002

(51) Int. Cl.[7] .............................................. G06F 19/00
(52) U.S. Cl. ........................................ 700/163; 264/16
(58) Field of Search ................................ 700/163, 159, 700/117, 118; 433/218, 183, 180, 34; 264/222, 16

(56) References Cited

U.S. PATENT DOCUMENTS

| | | | |
|---|---|---|---|
| 4,575,805 A | | 3/1986 | Moermann et al. |
| 4,663,720 A | * | 5/1987 | Duret et al. ................. 700/163 |
| 4,766,704 A | | 8/1988 | Brandestini et al. |
| 5,224,049 A | * | 6/1993 | Mushabac ................... 264/222 |
| 5,725,376 A | * | 3/1998 | Poirer ......................... 433/172 |
| 6,049,743 A | * | 4/2000 | Baba ........................... 700/163 |
| 6,482,284 B1 | * | 11/2002 | Reidt et al. .................... 264/16 |
| 6,512,994 B1 | * | 1/2003 | Sachdeva ...................... 433/24 |

OTHER PUBLICATIONS

Editor Werner H. Mörmann; Andreas Bindl, Björn Richter, Wiebke Apholt, Robert T. Toth; CEREC *Computer Aided Design Computer Integrated Manufacturing*, Full–Ceramic Crowns; CAD–CIM Library vol. 2 dated 1999.

* cited by examiner

*Primary Examiner*—Albert W. Paladini
(74) *Attorney, Agent, or Firm*—Merchant & Gould

(57) ABSTRACT

Methods and systems for developing a dental bridge through computer-aided design are shown and described. With reference to an image of the volume to fill with the bridge, a proposed dental bridge is shaped to fit between teeth adjacent to the volume to fill while being contoured to a profile line specifying the gum contour and the contour of surfaces of the adjacent teeth to be bonded. Retainers of the proposed bridge are shaped and positioned to abut the adjacent teeth. The data specifying the proposed bridge may be delivered to a milling machine where a blank is milled into the corresponding bridge. The bridge may then be installed by bonding the retainers to the adjacent teeth.

31 Claims, 14 Drawing Sheets

COMPUTER-AIDED DESIGN OF A PONTIC WITH RETAINERS

TECHNICAL FIELD

The present invention is related to the design of dental bridges. More particularly, the present invention is related to using computer-aided design in development and manufacture of a dental bridge that includes a pontic with retainers.

BACKGROUND

Dental bridges are used where a patient has a gap between two teeth. The gap forms an empty volume bounded by an adjacent tooth on each side and the gum line. The gap can result from an extracted tooth, a congenitally missing tooth, and other similar reasons. Conventionally, the adjacent teeth are ground down to make them suitable for crowns that adjoin the dental bridge and fix it in place when installed. The dental bridge is built by producing an artificial tooth that mounts to a frame, and the frame has the crowns attached to each side. The crowns are mounted on the teeth adjacent to the gap, and the artificial tooth between the two crowns fills the empty volume.

The conventional process requires that the adjacent teeth be ground even though they may be healthy teeth. Furthermore, the conventional process requires a relatively lengthy amount of time to prepare the bridge with the attached crowns. For example, a mold may be produced from the patient's mouth so that a manual process such as the lost wax technique may be used with the mold to make the framework for the bridge.

Computer-aided design has improved upon conventional approaches to designing and installing crowns. Computer imaging of the ground tooth to be crowned can be performed. From the computer image, computer-aided design software can propose a crown to fit the ground tooth and can communicate the design to a milling machine. The milling machine then mills a porcelain blank to produce the crown designed through the software.

One such computer aided design software is the CEREC family of software by Sirona Dental Systems. The CEREC family of software and machinery allows a dentist to image the area to crown, and the software analyzes the image to propose a crown to fit. The dentist may adjust the proposed crown as deemed necessary and then send the crown data to the milling machine of the CEREC system. The milling machine then mills the crown from a blank.

The current CEREC family of software is used to design a crown but lacks the functionality to propose and subsequently mill a complete dental bridge that is made up of a pontic to fill the empty volume and retainers to fix the pontic in place. A dental bridge including a pontic with retainers is a type of dental bridge that has retainers that may be bonded to the adjacent teeth. The retainer may be wing shaped for abutting an outer surface of an adjacent tooth, may be an in-lay to the adjacent tooth, may be a crown for the adjacent tooth, or other similar structure for attachment to adjacent teeth. Therefore; the adjacent teeth are not necessarily ground and fitted with a crown when installing the bridge unless the adjacent teeth are unhealthy.

The dental bridge including the pontic and retainers may be one continuous piece of ceramic without any additional support structure, thereby simplifying the construction of the bridge. Conventionally, a pontic with retainers is constructed in a manner similar in complexity to the conventional process for creating crowns. A mold may be taken and then from the mold, a model of the area may be made so that a manual process may be used to produce the pontic with retainers. This conventional process is lengthy and burdensome for the patient.

SUMMARY

Embodiments of the present invention provide methods and systems for using computer-aided design software to design bridges that are pontics with retainers. For one example, the CEREC software may be manipulated to enable design of a pontic with retainers. The manipulation of the CEREC software may occur through user intervention with the editing tools of the CEREC software to adapt structural details proposed by CEREC into a bridge structure. Alternatively, manipulation of the CEREC software to adapt to a bridge structure may occur through programming patches to the CEREC software that cause automatic adaptation of the details when selected by a user.

Embodiments of the present invention involve various steps for creating the dental bridge. The volume to fill with the bridge and at least portions of the adjacent teeth are imaged. A pontic with retainers is then specified in relation to the image so that the pontic fits in the volume and the retainers abut surfaces of the adjacent teeth. Generally, a computer executes the steps to create the proposed dental bridge as discussed above either automatically or through user interaction with an existing computer-aided design software such as CEREC.

The proposed dental bridge may be designed by shaping a bottom line of the proposed bridge so that it defines the shape of the base of the bridge including the pontic and retainers. The elevation of the bottom line is contoured to a profile line taken from the image data that specifies the gum line and the elevation of the surfaces of adjacent teeth where the retainers will fit. A proximal contact line is shaped and positioned to define a proximal area of the pontic that fits between the adjacent teeth and the retainers that abut the adjacent teeth. The proximal contact line is positioned to have an elevation above the bottom line. A labio-lingual line is shaped and positioned to define a labio-lingual area of the pontic that fits between the adjacent teeth and the retainers that abut the adjacent teeth. The labio-lingual line is positioned to have an elevation above the proximal contact line. An incisal line is shaped and positioned to define an incisal surface for at least the pontic which fits between the adjacent teeth. The bottom line, proximal contact line, labio-lingual line, and incisal line define a proposed dental bridge that is a pontic with retainers, and the data of the proposed bridge is used to mill the actual bridge from a blank.

The various aspects of the present invention may be more clearly understood and appreciated from a review of the following detailed description of the disclosed embodiments and by reference to the drawings and claims.

DETAILED DESCRIPTION

Embodiments of the present invention generally involve computer-aided design of dental bridges. A dental bridge that is a pontic with retainers is useful for reasons such as it may be bonded to adjacent teeth without necessarily requiring the adjacent teeth to be crowned. Additionally, the dental bridge may be formed as a unitary structure rather than having an additional support structure. The dental bridge can be designed and manufactured using computer imaging and computer-aided design.

The present invention is described in the context of a CEREC computer program. One skilled in the art will appreciate that CEREC is an exemplary computer program used for illustrative purposes only and that other programs or computer systems may alternatively be used and fall within the scope of the present invention.

Figure 1:
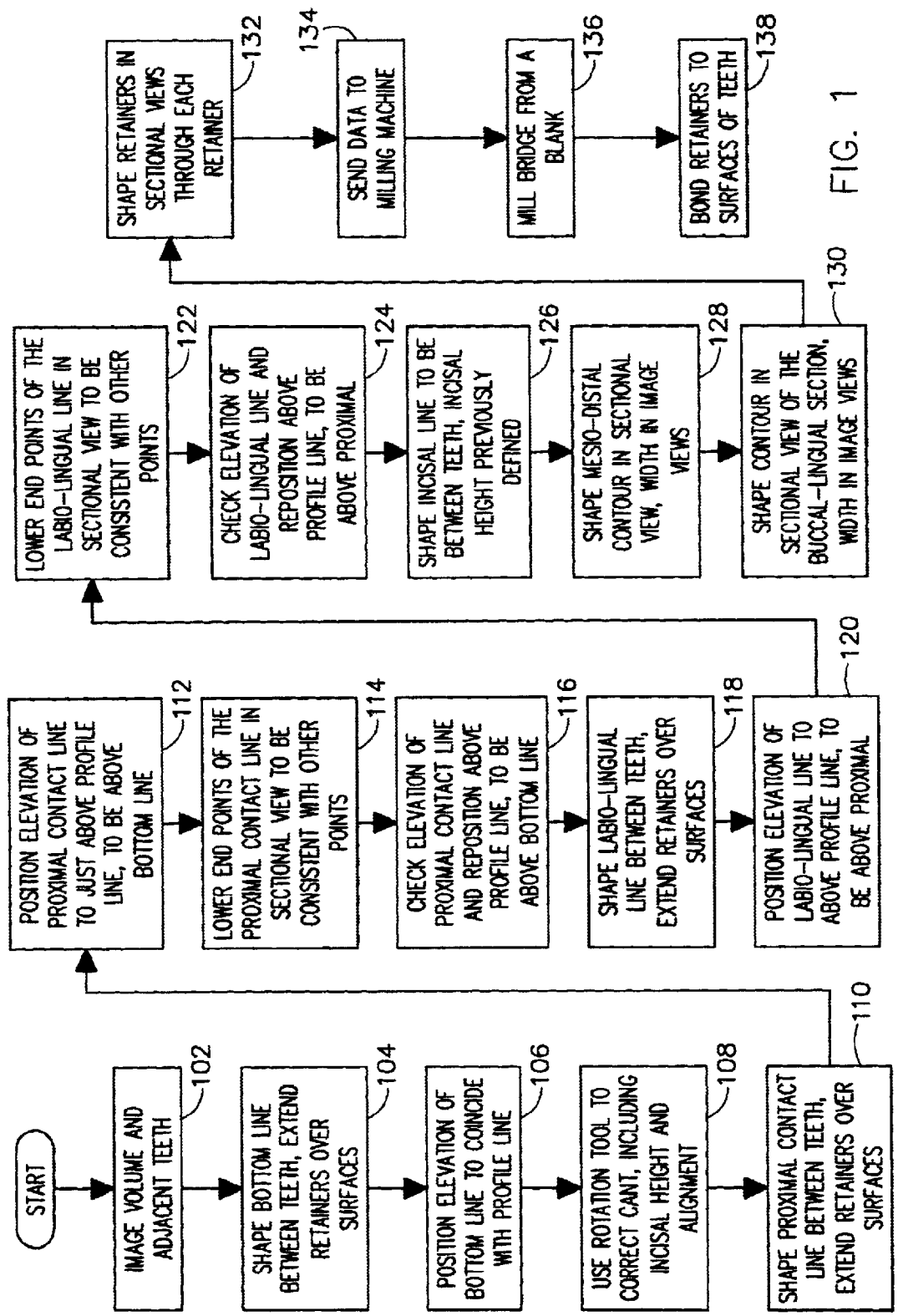
FIG. 1 shows a flow chart demonstrating the logical operations of an embodiment for developing and manufacturing a dental bridge utilizing computer-aided design.
Figure 2:
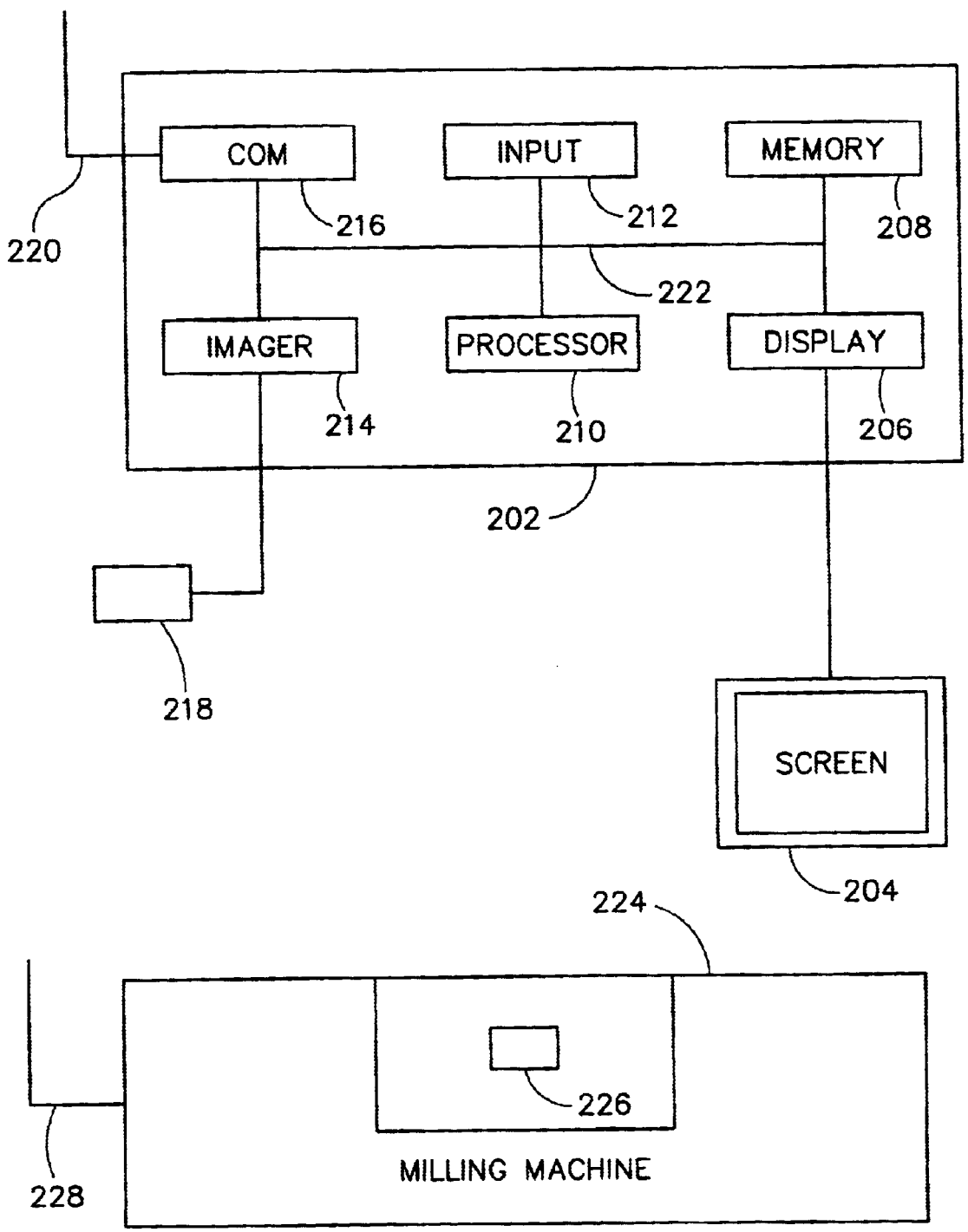
FIG. 2 is a diagram of a computer system for implementing the embodiment of FIG. 1.

FIG. 1 shows an operational flow of the logical operations required to design, manufacture, and install a dental bridge. The logical operations of FIG. 1 are implemented on a computer system such as shown in FIG. 2. The CEREC computer milling system, as noted above, is one example of a computer system as shown in FIG. 2. The computer system includes a computer 202 that has several components. A processor 210, such as a general-purpose programmable processor or hard-wired logic, is included to perform the processing steps of the logical operations. The processor 210 communicates through a bus 222 with other devices.

The image data that is created of the patient's mouth is generally stored in a memory device 208 such as random access memory. The processor 210 can access the image data from the memory 208 as needed and can write data to memory 208 during the design process, including the data generated to define the dental bridge. The processor 210 communicates with an imaging device 214 over the bus 222.

The imaging device 214 controls a camera 218. Generally, the camera 218 is proportioned so that it may extend into the mouth of the patient and suspend over the location where the bridge is to be installed. The camera 218 takes a still image of the location and provides image data to the imager 214. The imager 214 makes the digital image data available to the processor 210 for use during the computer-aided design process.

During the computer-aided design process, it is generally desirable to permit user interaction. An input device 212 such as a mouse and/or keyboard allows the user to provide input to the processor 210 to initiate the design process. The processor 210 implements within the design process the selections and alterations that the user makes. To allow the user to view the design process taking place, the processor 210 communicates with a display adapter 206 that provides display signals to a display screen 204. The computer-aided design program being executed by the processor 210 provides a graphical user interface on the display screen 204, and the user interacts with the interface accordingly through the input device 212.

Once the proposed bridge design has been completed on the computer 202, the processor 210 transfers the data specifying the proposed bridge to a communication device 216 that communicates the data to a milling machine 224. The transfer of data from the computer 202 to the milling machine 224 may be done over a wired connection such as a direct line, a local area or wide area network, or wirelessly. Likewise, one computer may obtain the image data and transfer it to a second computer, such as over a network or via a portable disc, so that the design may be performed on the second computer. The design data may then be transmitted directly from the second computer to the milling machine 224 or may be transmitted back to the first computer and then to the milling machine.

As shown, the computer 202 transmits the data from an antenna 220, and the milling machine 224 receives the data through an antenna 228. Radio frequency signals or other electromagnetic signaling may be used to carry the data from antenna 220 to antenna 228. The milling machine 224 takes the data and mills a blank 226. The blank 226 begins as a solid box made of a material such as a ceramic and preferably porcelain. The milling machine 224 mills the box according to the proposed bridge data to convert the box shape into a dental bridge that has a shape matching the shape of the proposed dental bridge. The dental bridge can then be installed in the patient's mouth. The entire process from imaging to milling and installation can be done during a single patient session.

Again with reference to FIG. 1, the design process of the dental bridge begins at image operation 102. Here, the computer 202 captures the image of the location in the patient's mouth where the bridge will be installed. The image includes the volume to fill with the bridge bounded by the gum of the patient and at least portions of the adjacent teeth. The image data is shown on the display screen 204 within a window of the graphical user interface.

Figure 3:
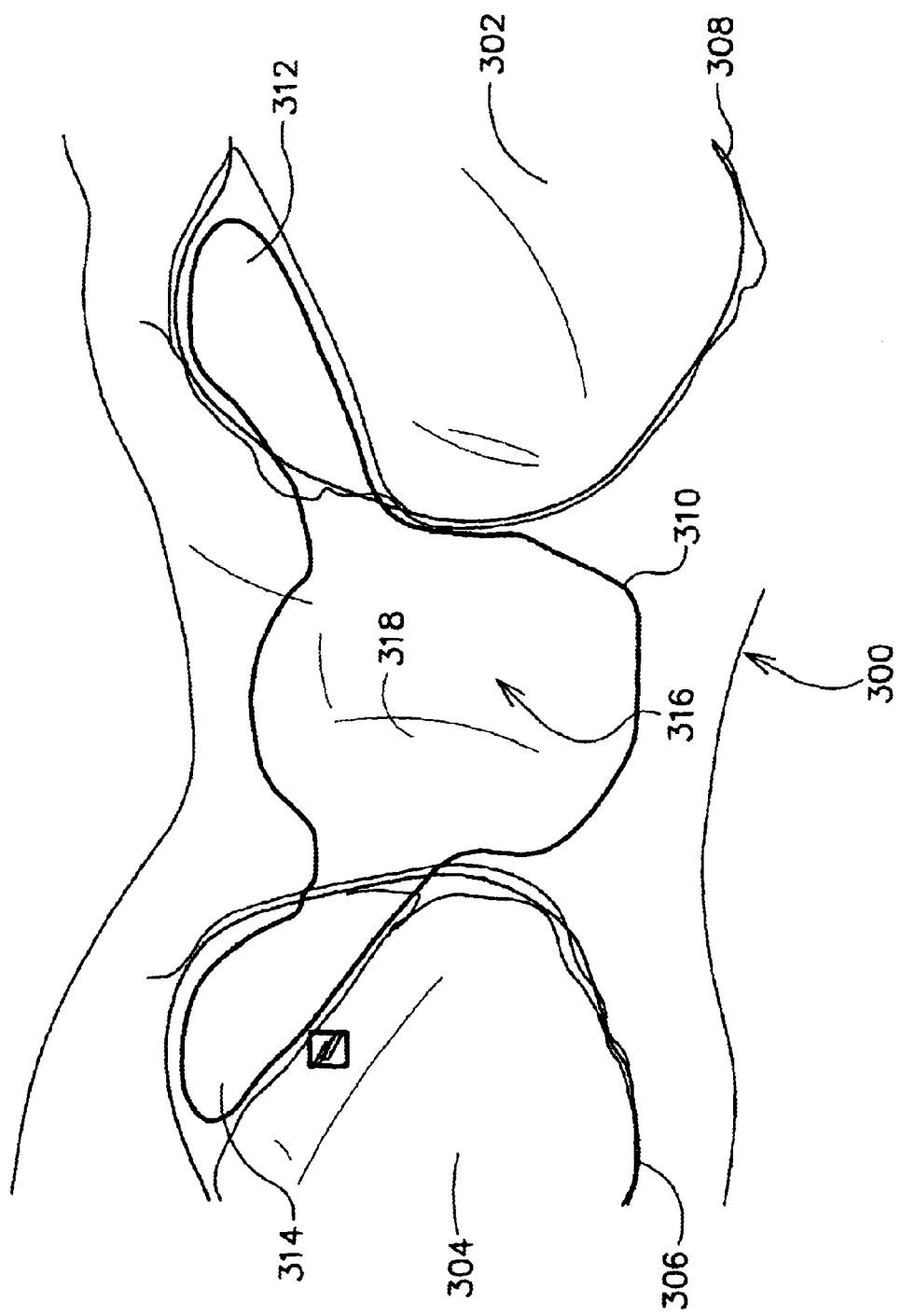
FIG. 3 is a screen shot from the CEREC 3 software showing an image of the volume being filled with the pontic having retainers and showing a shaped bottom line of a proposed dental bridge that is the pontic and retainers.

Once the CEREC 3 program being executed on the computer 202 accesses the image data, the user can select from a program menu a crown selection that causes the CEREC 3 program to propose a crown based on the image data. The CEREC 3 program displays the image data, and the user can control a draw tool of the program to at least partially draw a line around the periphery of the adjacent teeth that appears superimposed on the image data. The line is drawn without completely encircling the adjacent teeth. FIG. 3 shows the contents of a CEREC 3 window 300 displaying the image data.

A gum 318, an adjacent tooth 302, and another adjacent tooth 304 bound the volume 316 that will receive the bridge in this example where the retainers will be wing shaped to abut lingual surfaces of the adjacent teeth 302, 304. The user draws the line 306 partially around tooth 304 and draws line 308 partially around tooth 302. The CEREC 3 program then proposes a bottom line that is superimposed on the image. The bottom line is a line that specifies the shape and elevation of the base of the piece being designed. The CEREC 3 program is expecting to design a crown, so the proposed base is expected to abut the top of a tooth prepared to receive a crown and have peripheral dimensions of a normal tooth. However, for the dental bridge utilizing a pontic with retainers, the base should abut or reside slightly above the gum line of the patient and should have retainers that extend onto surfaces of the adjacent teeth, typically the lingual surface for wing shaped retainers.

Because the currently available CEREC 3 program is attempting to automatically design a crown, the proposed bottom line is unsatisfactory because it does not provide the retainers necessary for the dental bridge. Therefore, at shape operation 104, the user manipulates the shape of the bottom line as shown in FIG. 3 to provide retainers that are wing shaped in this example. The shaped bottom line 310 fills the area between the adjacent teeth 302, 304 and also provides retainers 312, 314 that cover the lingual surfaces of the adjacent teeth 302, 304 in this example. Other surfaces such as the facial and occlusal surfaces of the adjacent teeth may be used to bond the retainers in situations where appropriate.

Once the bottom line 310 has been shaped to add the retainers 312, 314, the user positions the bottom line relative to the profile line at position operation 106. The elevation of the bottom line is positioned so that the pontic portion coincides with the gum line portion of the profile line contour and the retainer portions coincide with the profile line contour that represents contour of the surfaces of the adjacent teeth to be bonded.

Figure 4:
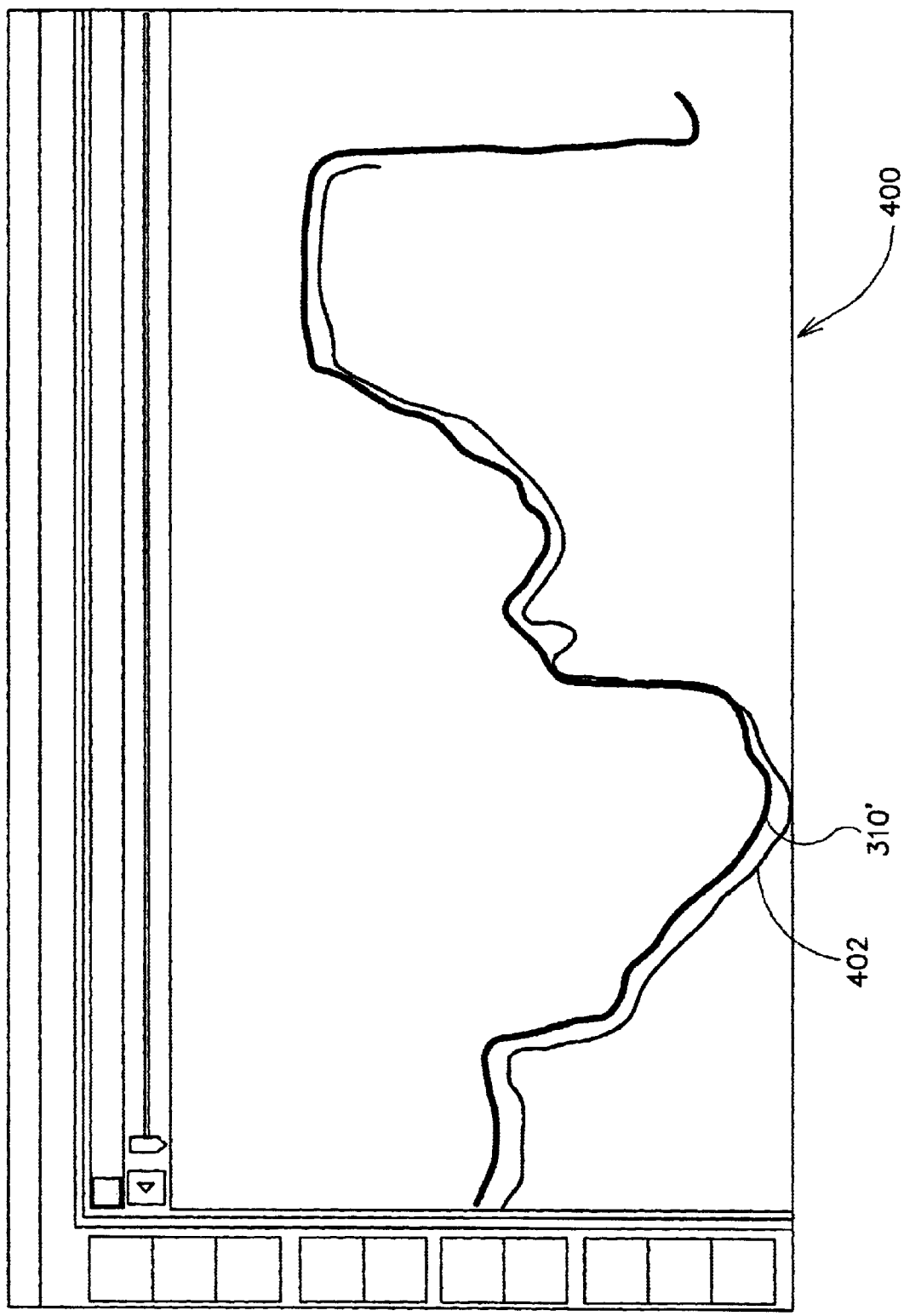
FIG. 4 is a screen shot from the CEREC 3 software showing the elevational position of the bottom line relative to the contour of the profile line in a projection view.

FIG. 4 is a screen shot 400 showing a projection view of the bottom line 310' positioned relative to the profile line 402. In FIG. 4, the projection view demonstrates the elevation as viewed through rotation around an axis at the center of the base defined by the bottom line. As shown, the bottom line 310' is positioned on or slightly above the profile line 402. It should be noted that the projection and sectional views discussed herein are zoomed in to emphasize detail, and the lines present in these views have been enhanced for clarity.

Figure 5:
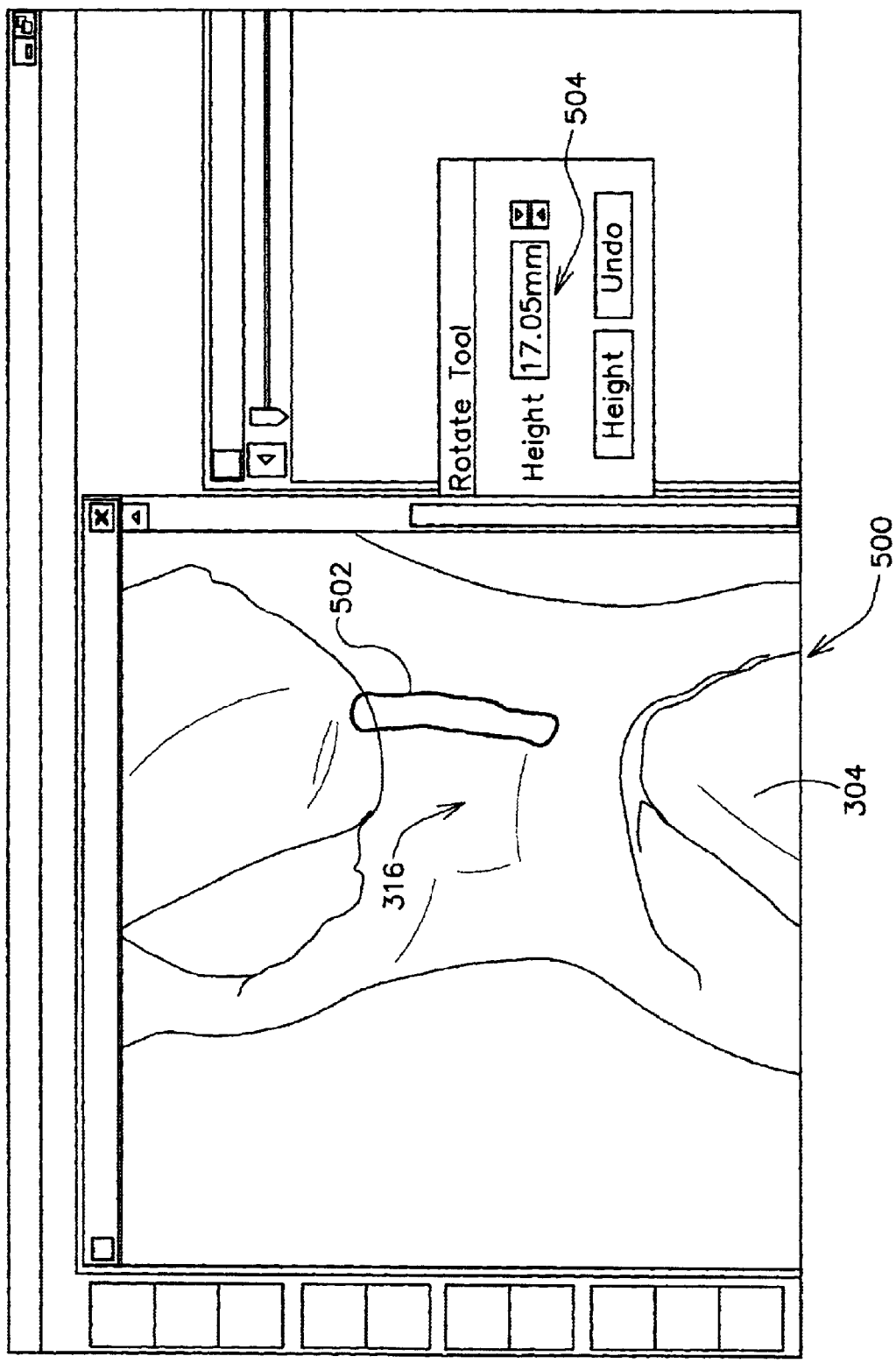
FIG. 5 is a screen shot from the CEREC 3 software showing use of a rotation tool to edit a cant and elevation of the proposed bridge.

After the bottom line 310' has been positioned at the proper elevation, the user reviews a proposed incisal edge line 502 (FIG. 5) demonstrating the height and alignment of the bridge at cant operation 108. The incisal edge line 502 is shown in a screen shot 500 of FIG. 5. Using a rotation tool 504 of CEREC 3, the user can correct the cant of the bridge by adjusting the height and alignment of the incisal edge line 502 relative to the adjacent teeth 302, 304.

Figure 6:
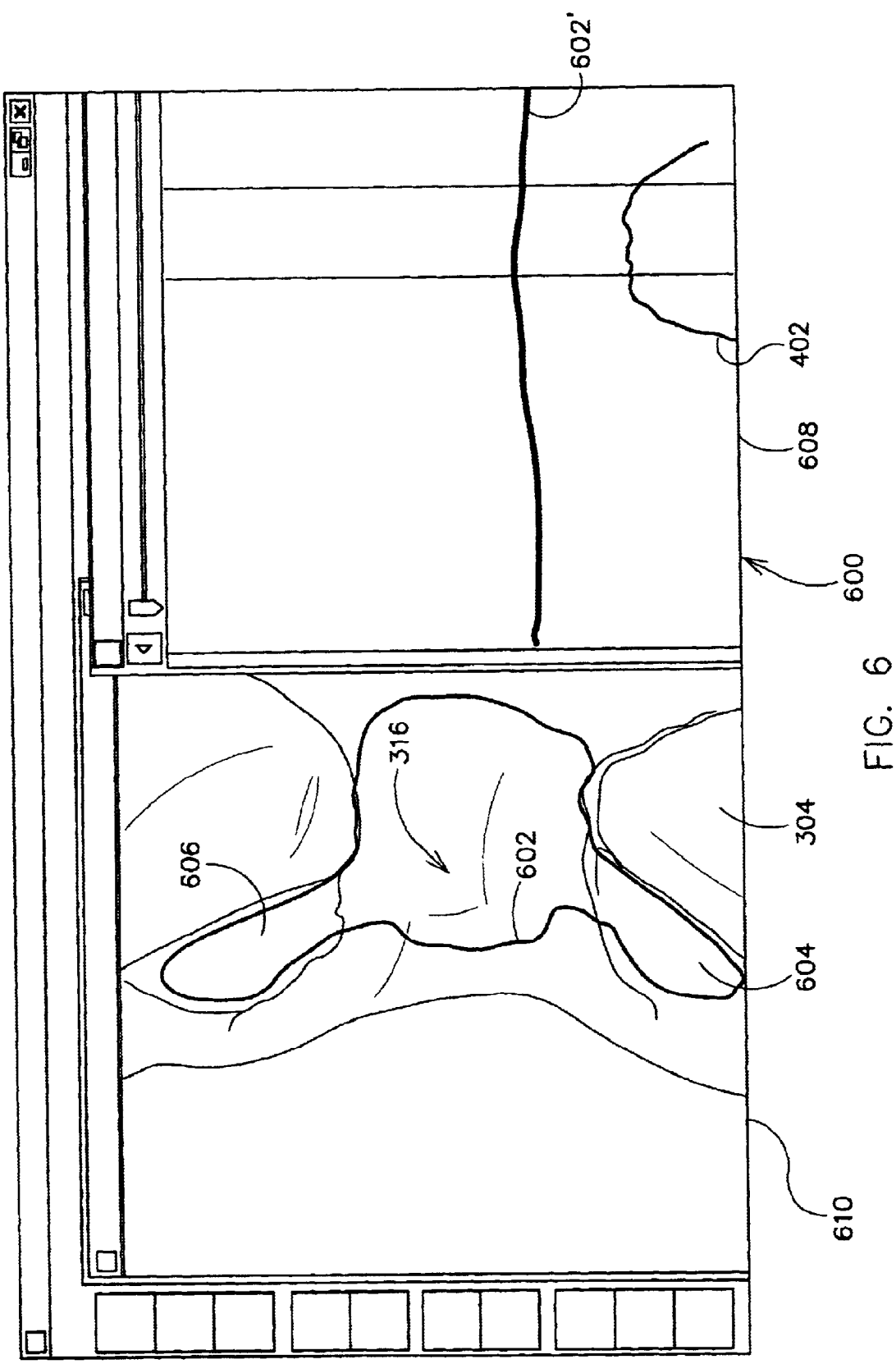
FIG. 6 is a screen shot from the CEREC 3 software showing a shaped proximal contact line of the proposed bridge in relation to the image.

CEREC proposes a proximal contact line that defines the periphery of the piece at an elevation above the bottom line. Again, because the currently available CEREC software is attempting to propose a crown, the proposed proximal contact line is unsatisfactory because it fails to adequately specify the retainers and has an improper elevation relative to the profile line 402 and bottom line. Therefore, the user shapes the proximal contact line at shape operation 110 into a form such as shown in the screenshot 600 of FIG. 6 providing a image view window 610 and a projection view window 608.

The proximal contact line 602 once shaped defines the middle periphery of retainers 604 and 606 that are positioned over the lingual surfaces of the adjacent teeth 302, 304. However, as shown in the projection window 608, the elevation of the proximal contact line 602' is too high relative to the profile line 402. To correct the elevation, the user positions the proximal contact line 602' at an elevation that is just above the profile line 402 at position operation 112. Thus, the proximal contact line 602' is positioned at an elevation just above the bottom line previously positioned. The new position of the proximal contact line is shown as proximal contact line 702 in the projection view of screen shot 700 of FIG. 7. The new proximal contact line 702 has a position below that of the proposed proximal contact line 602', and the new proximal contact line 702 is contoured to the profile line 402.

Figure 7:
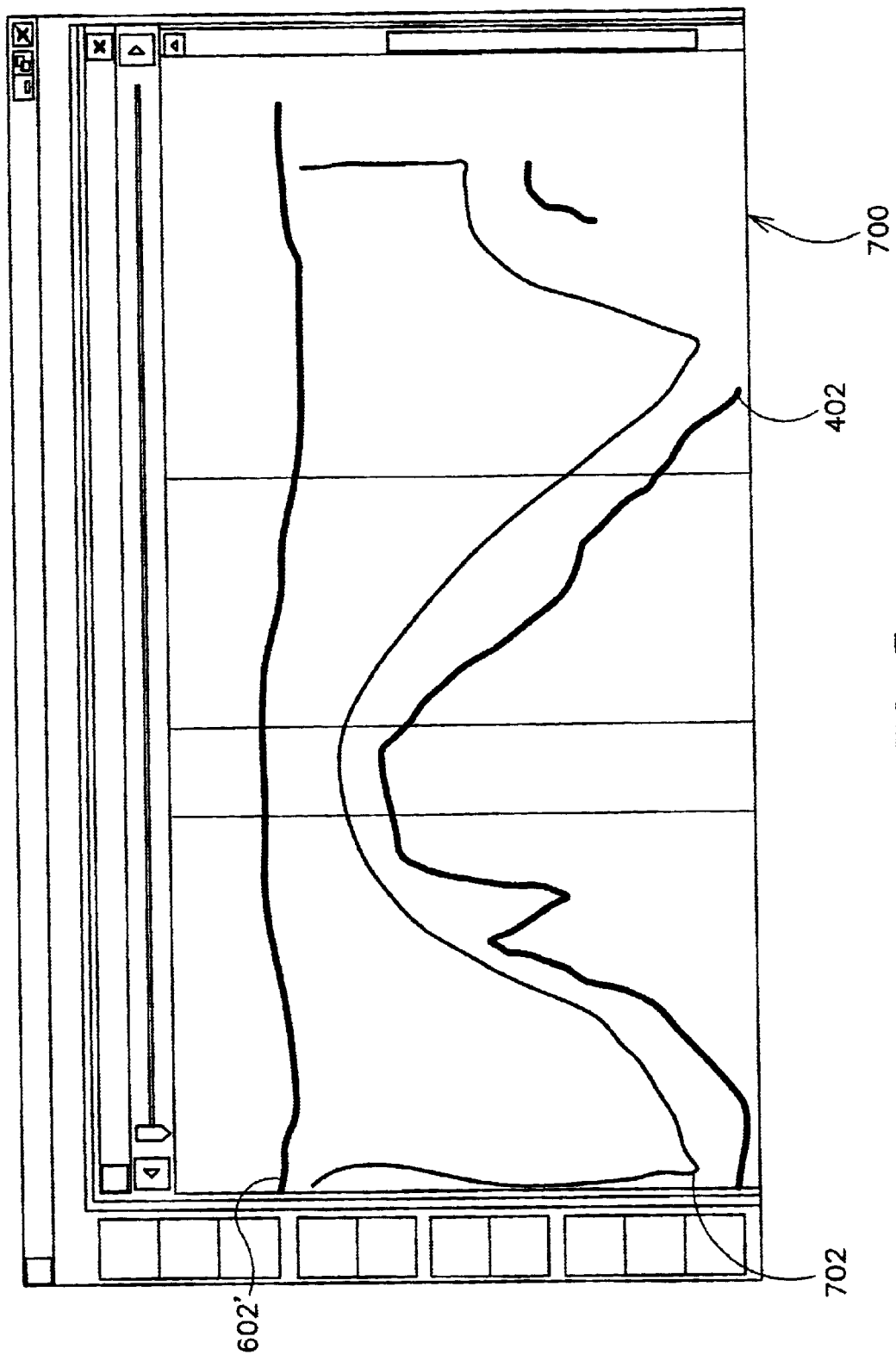
FIG. 7 is a screen shot from the CEREC 3 software showing the elevational position of the proximal contact line relative to the contour of the profile line in a projection view.
Figure 8:
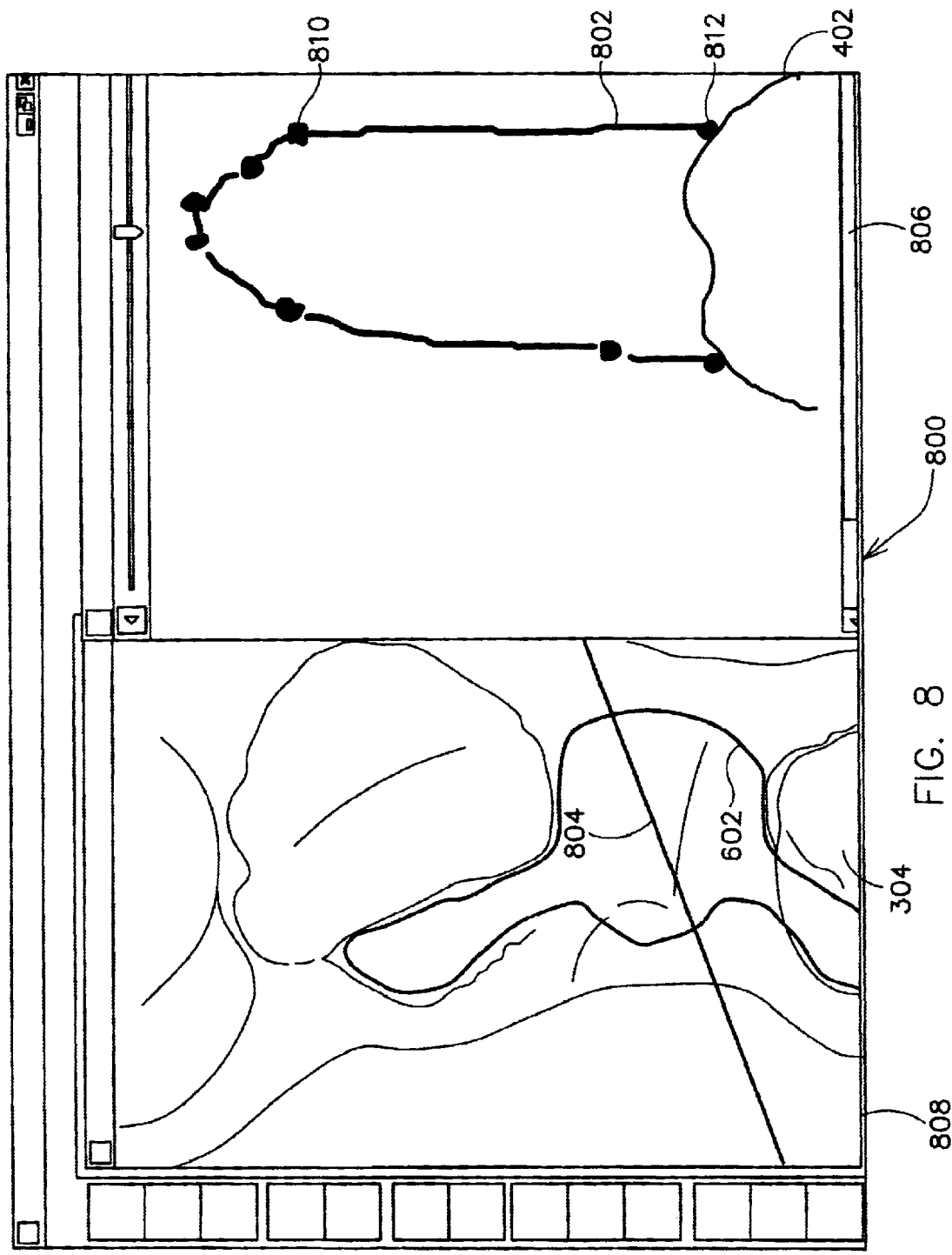
FIG. 8 is a screen shot from the CEREC 3 software showing two juxtaposed views of the proximal contact line to demonstrate editing of endpoints of the proximal contact line through a sectional view that is across the widest diameter and through the endpoint.

As shown in FIG. 7, when positioning the proximal contact line 602' closer to the profile line 402, the endpoints in view of the new proximal contact line 702 cannot be lowered in projection view. Therefore, the user switches to sectional view to lower the endpoints at end-point operation 114. The section is taken through the widest diameter of the proximal contact line 602 at the endpoint in the image view. The screenshot 800 of FIG. 8 shows an image view window 808 and the corresponding sectional window 806.

The section is taken through line 804 across the proximal contact line 602 at the endpoint. The bridge periphery 802 of the sectional view contains points indicating the elevation of the bottom line and proximal contact line previously discussed as well as a labio-lingual line and an incisal line that are discussed below. The point 810 shows the end point of the proximal contact line at an elevation that is too high relative to the profile line. Therefore, the user moves the point 810 of the proximal contact line 702 down to just above the bottom line point 812 residing on the profile line 402.

Figure 9:
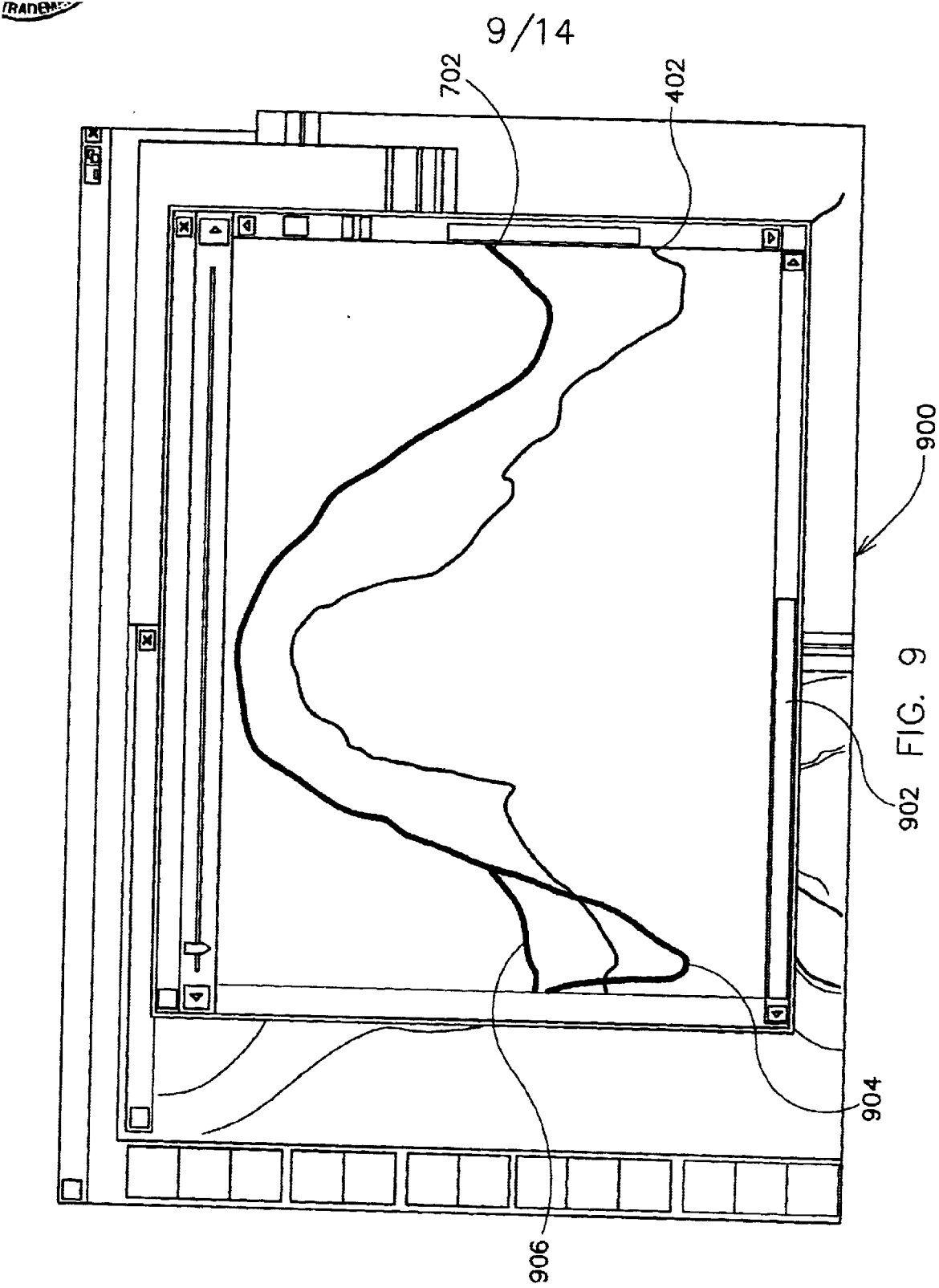
FIG. 9 is a screen shot from the CEREC 3 software showing additional positioning of the proximal contact line to provide an elevation above the profile line in a projection view.

After correcting the endpoints, the user verifies in projection view that all points of the proximal contact line 702 are positioned sufficiently above the profile line 402 at reposition operation 116. As shown in screenshot 900 of FIG. 9, the projection view window 902 shows that the proximal contact line 702 has a portion 904 that has dropped below the profile line 402 due to lowering the end point in sectional view. The user repositions the section 904 to the position shown as section 906, which has an elevation sufficiently-above the profile line 402.

Figure 10:
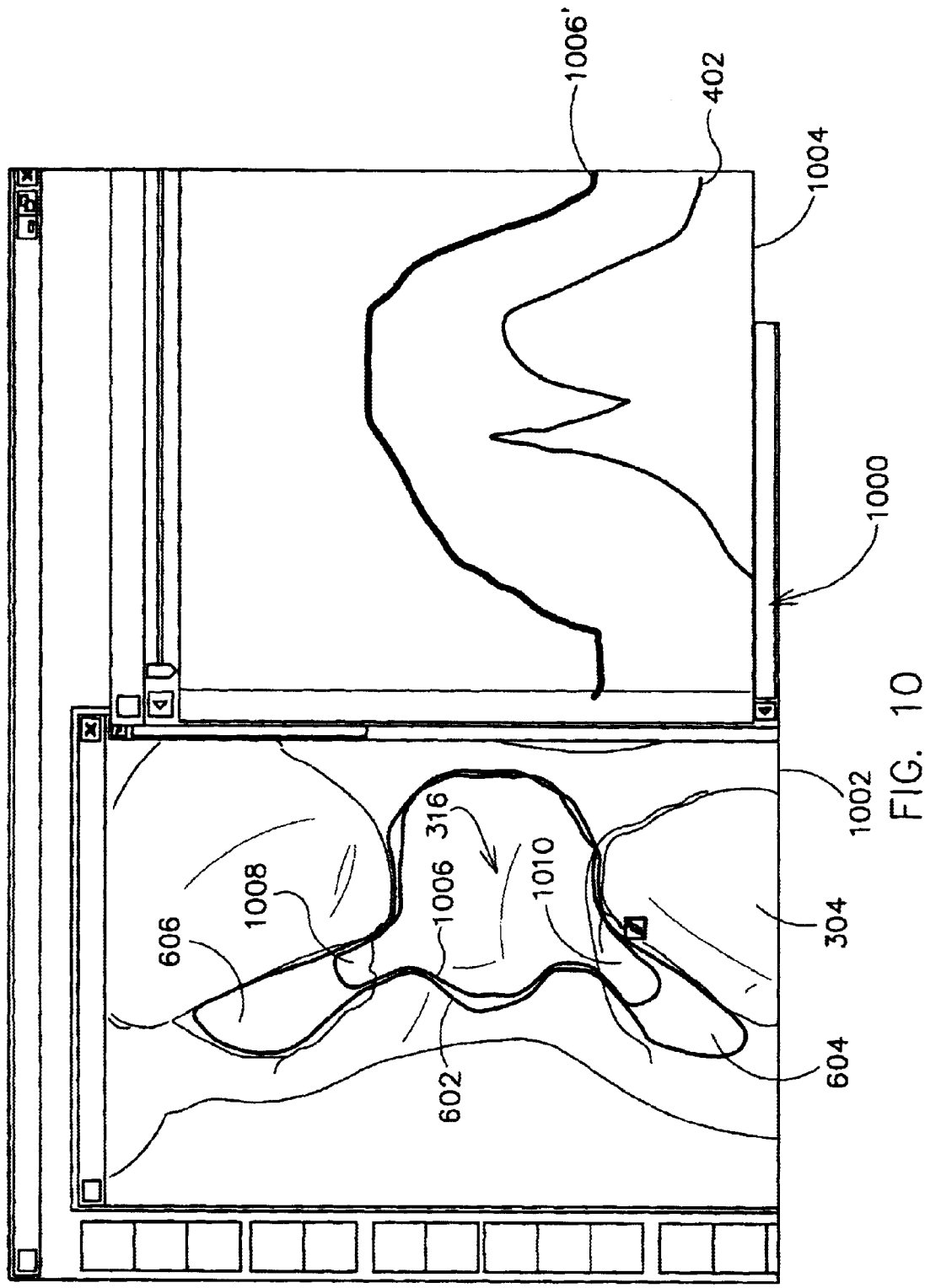
FIG. 10 is a screen shot from the CEREC 3 software showing two juxtaposed views of the labio-lingual line illustrating shape in the image view and elevation in the projection view.

CEREC proposes a labio-lingual line that has an elevation above the proximal contact line 702. The proposed labio-lingual line is also flawed because the currently available CEREC software is proposing a crown instead of a bridge that is a pontic with retainers. Therefore, the user shapes the labio-lingual line at shape operation 118. As shown in the image view window 1002 of screenshot 1000 in FIG. 10, the labio-lingual line 1006 is shaped to include retainers 1008 and 1010 that are positioned over the lingual surfaces of the adjacent teeth 302, 304. However, these retainers 1008, 1010 are smaller than the retainers 604, 606 of the proximal contact line 602 and the retainers 312, 314 of the bottom line 310. The retainer design lines 1008, 1010 are smaller because the labio-lingual line 1006 has an elevation that is closer to the incisal surface of the bridge, and it is desirable to reduce the retainer structure away from the pontic but still provide additional strength and bulk to the junction of the retainers with the pontic where most stress will occur.

The labio-lingual line 1006' of the projection view window 1004 has been placed by the user at position operation 120 at an elevation closer to the profile line 402 than was originally proposed by CEREC, but it is positioned at an elevation higher than the proximal contact line 702. Although not shown in FIG. 10, the endpoints of the labio-lingual line cannot be positioned lower in projection with the other points of the line. Therefore, the labio-lingual line 1006' is manipulated in a fashion similar to the proximal contact line 702 to correct the problem.

The user lowers the end points of the labio-lingual line in a sectional view taken across the widest diameter of the labio-lingual line at the endpoint at end point operation 122. This process resembles the correction shown for the proximal contact line point 810 in FIG. 8. Then at reposition operation 124, the user checks the elevation of the labio-lingual line 1006' in projection view to maintain the labio-lingual line at an elevation sufficiently above the profile line. This process resembles the correction shown for the proximal contact line 702 in FIG. 9.

Figure 11:
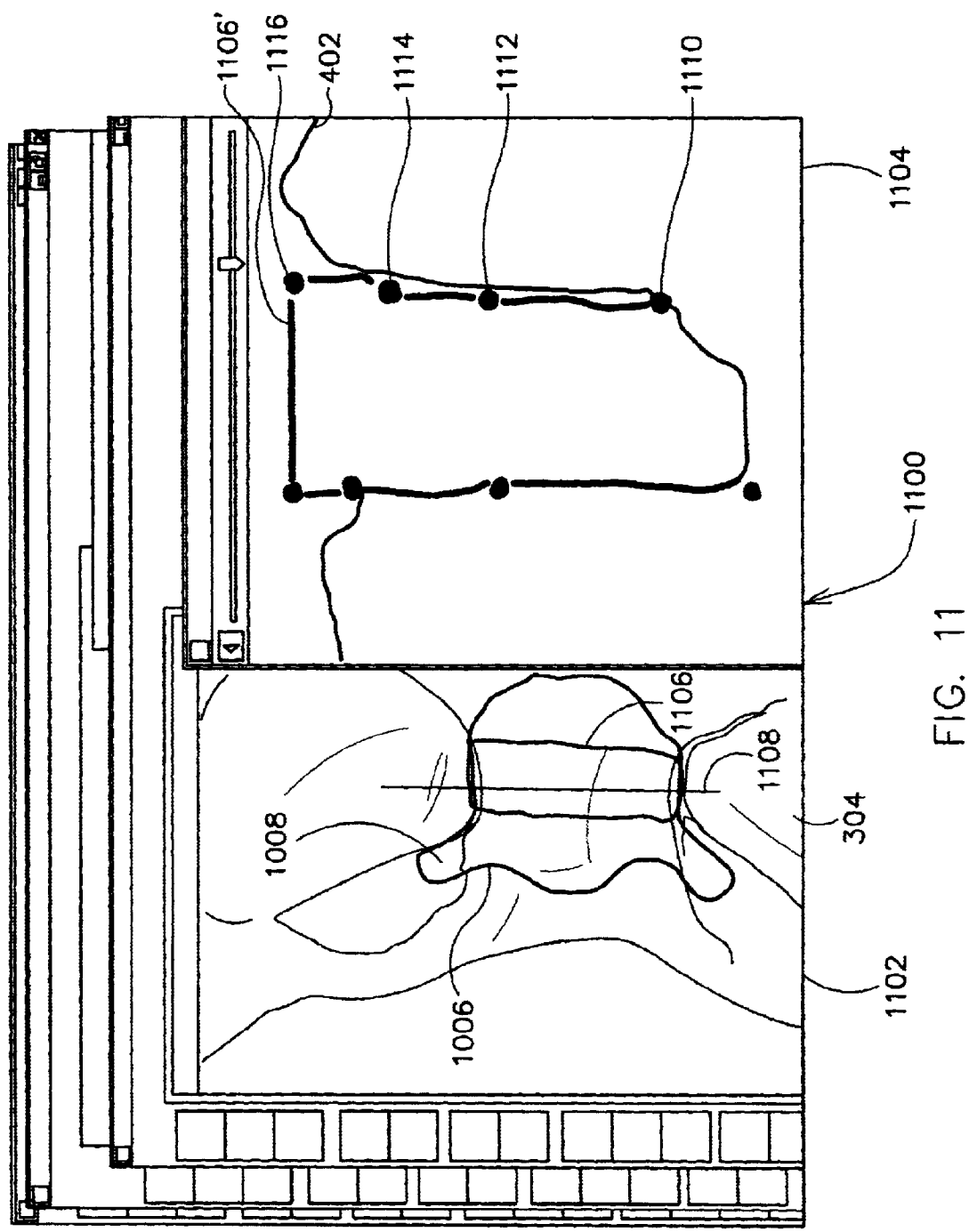
FIG. 11 is a screen shot from the CEREC 3 software showing two juxtaposed views of the incisal line illustrating shape relative to the labio-lingual line in the image view and elevation in the sectional view.

CEREC proposes an incisal line. The height of the incisal line has previously been defined at cant operation 108. As shown in the image view window 1102 of the screenshot 1100 of FIG. 11, the user shapes the incisal line 1106 to have sufficient width to fill the space between the two adjacent teeth 302, 304 and to have a thickness that is consistent with the incisal surface thickness of the adjacent teeth 302, 304.

To shape the medio-distal contour, a sectional view through a longitudinal line 1108 of the incisal line 1106 may be provided in a sectional window 1104 of the screenshot 1100. The user may slightly move up or down the proximal contact line point 1112, labio-lingual line point 1114 and/or the incisal line point 1116 on either side of the bridge to adjust the medio-distal contour at contour operation 128. The bottom line point 1110 is fixed. The incisal surface 1106' appears in the sectional view through the incisal line 1106. The width of the medio-distal section may be altered by manipulation of the proximal contact line, labio-lingual line, and incisal line in the image view for each of those lines.

Figure 12:
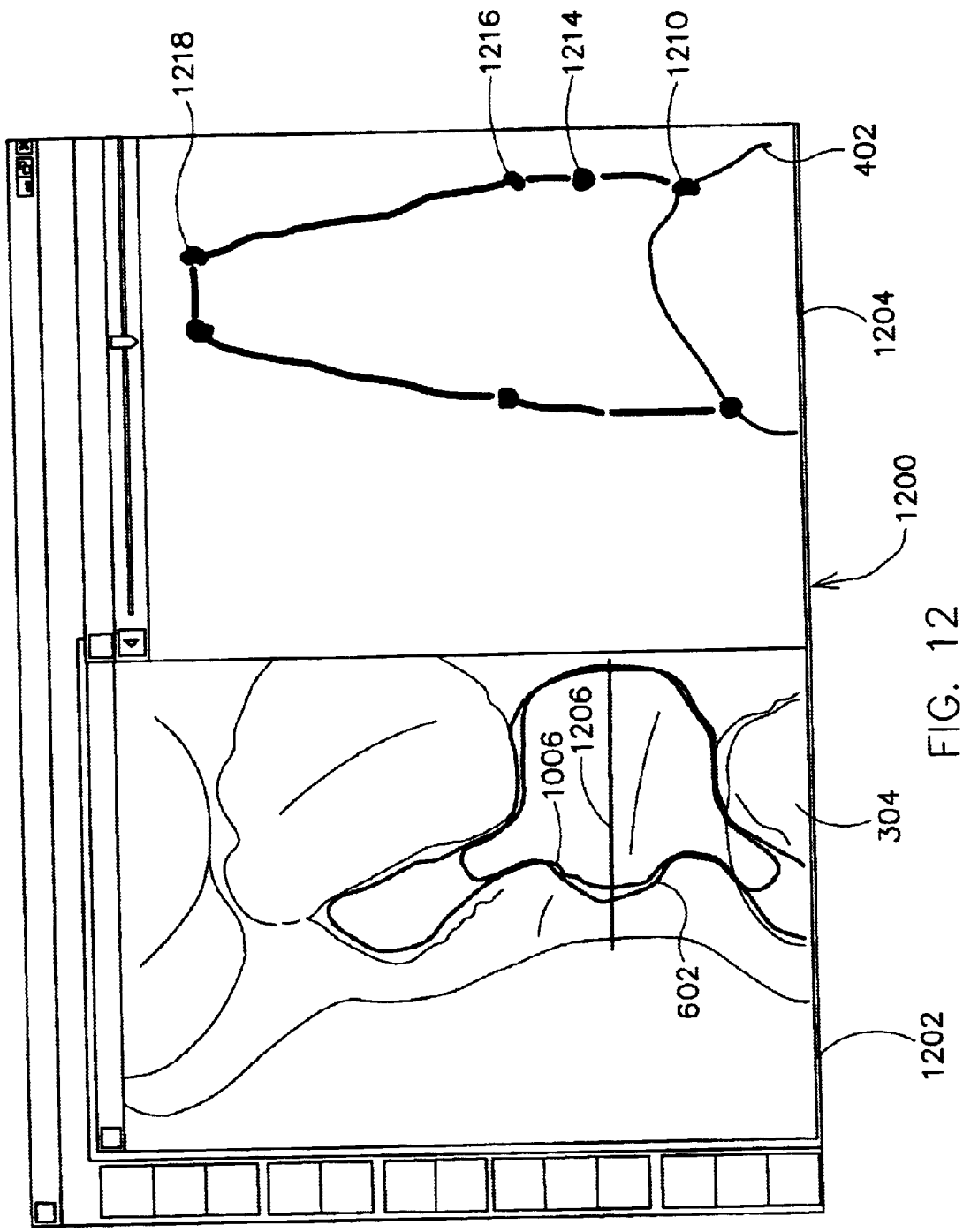
FIG. 12 is a screen shot from the CEREC 3 software showing two juxtaposed views of the proposed dental bridge to illustrate the buccal-lingual section in a sectional view.

The contour in the buccal-lingual section may be shaped in a sectional view through a sectional line 1206 as shown in a sectional window 1204 of the screenshot 1200 of FIG. 12. The sectional line 1206 is shown in the image view window 1202 of the screenshot 1200. The user may slightly move up or down the proximal contact line point 1214, labio-lingual line point 1216 and/or the incisal line point 1218 on either side of the bridge to adjust the buccal-lingual contour at contour operation 130. The bottom line point 1210 is fixed. The width of the buccal-lingual section may be altered by manipulation of the proximal contact line, labio-lingual line, and incisal line in the image view for each of those lines.

Figure 13:
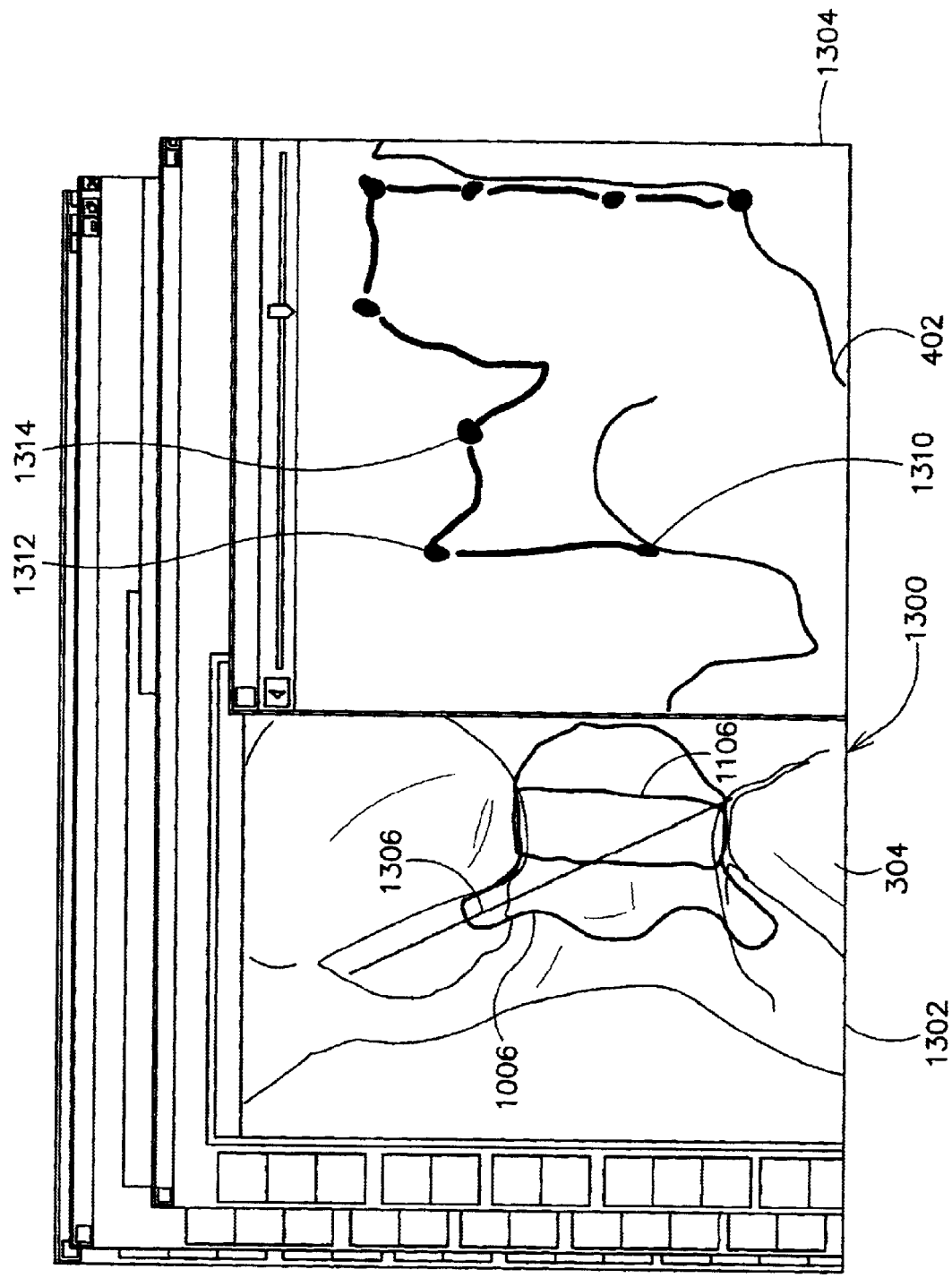
FIG. 13 is a screen shot from the CEREC 3 software showing two juxtaposed views of the proposed dental bridge to illustrate the retainers in a sectional view.

To shape the contour of the retainers, a sectional view may be taken through the longitudinal line 1306 passing through one retainer as shown in the image view window 1302 of screenshot 1300 in FIG. 13. The user may slightly move up or down the proximal contact line point 1312 and/or the labio-lingual line point 1314 to adjust the retainer contour at contour operation 132. The bottom line point 1310 is fixed. As shown, the proximal contact line point 1312 is too high relative to the labio-lingual line point 1314, and the user should move the proximal contact line point 1312 down to make a smoother retainer contour. Although only a few data points are manipulated when moving a point in section, the wing shaped retainer's width is minimal and those few data points refine the entire retainer volume. The width of the retainer section can also be altered by manipulation of the proximal contact line and labial lingual line in the image view for each of those lines.

It should be noted that the incisal line could also be used to define an upper portion of the retainers in the incisal line image view, especially for bridges where the incisal line actually represents an occlusal surface of the bridge and where an in-lay or crown is used as the retainer. For bridges having a winged shaped retainer and an incisal surface, patients may prefer that the retainers not be formed as part of the incisal surface for comfort.

At this point in the operational flow of FIG. 1, the proposed dental bridge is complete and is ready to be milled to form an actual dental bridge. The computer 202 sends the data of the proposed bridge to the milling machine 224 at send operation 134. After receiving the data, the milling machine 224 mills the porcelain blank into the bridge at mill operation 136.

After the bridge has been milled, the dentist may polish and apply various finishing procedures to the bridge and can install the bridge on the patient at bond operation 138. The dentist places the bridge in the volume to fill with the base of the bridge close to the gum line. The dentist uses a bonding process, such as resin bonding, to adhere the retainers of the bridge to the surfaces of the adjacent teeth. The bonding process may also be used to bond the pontic portion of the bridge to the proximal surfaces of the adjacent teeth. Typically, the lingual surface of the adjacent teeth is used to bond the bridge with wing shaped retainers as shown and the proximal surfaces of the pontic are bonded to the proximal surfaces of the adjacent teeth. However, as discussed above, facial and/or occlusal surfaces may also be used for bonding retainers such as where a retainer is a crown or in-lay or where a wing shaped retainer is designed to overlap the facial surface.

Figure 14:
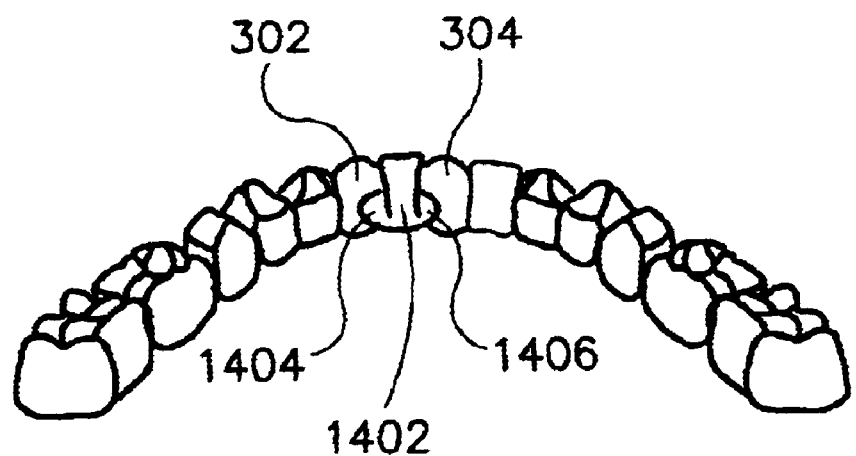
FIG. 14 is a view of the lingual surface of a patient's teeth including an installed dental bridge.
Figure 15:
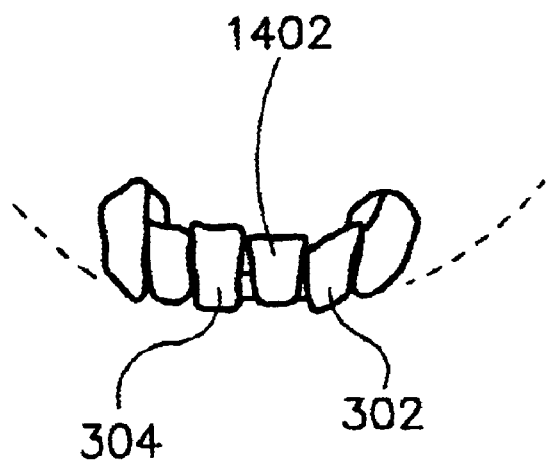
FIG. 15 is a view of the buccal/labial surface of the patient's teeth including the installed dental bridge.

The installed bridge 1402 is shown in FIG. 14. The bridge 1402 has retainers 1404 and 1406. Retainer 1404 is bonded to the lingual surface of the tooth 302. Retainer 1406 is bonded to the lingual surface of the tooth 304. The bridge 1402 may also be bonded to the proximal surfaces of the adjacent teeth 302, 304. As shown in FIG. 15, the dental bridge 1402 appears as a normal tooth on the labial surface.

It should be noted that the logical operations of FIG. 1 that have been described as user actions in the currently available CEREC 3 can be automated through a program patch to the CEREC 3 software. One of ordinary skill in the art will appreciate that the logical operations can be implemented through programming the steps into the program patch. Providing a dental bridge option within CEREC 3 through the program patch is preferred so that the user may select whether CEREC 3 should attempt to automatically design a dental bridge as opposed to the other restorations that are possible. However, if automated it remains preferable to allow user interaction to alter the proposed design as deemed necessary and/or to guide the automated process to completion.

Additionally, it should be noted that many of the logical operations of FIG. 1 are optional. For example, adjusting the cant, the mesio-distal contour, the buccal-lingual contour, and the retainer contour improve the appearance of the bridge. However, a functional bridge does not require that the cant or various contours be ideal. Thus, one of ordinary skill in the art will appreciate that many of these logical operations may be modified or omitted altogether.

Also, the logical operations and screenshots above show the use of the bottom line, proximal contact line, labio-lingual line, and incisal line. One skilled in the art will recognize than other numbers of lines may be used to specify the proposed dental bridge and that these four lines are shown and described for exemplary purposes only.

Although the present invention has been described in connection with various exemplary embodiments, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed is:

1. A method of creating a dental bridge using a CEREC program, comprising:
   imaging a volume to fill with the dental bridge along with at least portions of adjacent teeth on both sides of the volume to produce image data regarding the volume to fill;
   shaping and positioning a bottom line specifying a proposed dental bridge in the CEREC program from the image data so that the bottom line defines a shape of the base of the proposed dental bridge that fits between adjacent teeth bounding the volume, with the shape of the base including retainers that abut a surface of the adjacent teeth and with the bottom line elevation specified relative to a profile line from the image data so that the base of the proposed dental bridge resides on or above the gum line and the surface of the adjacent teeth to be bonded;
   shaping and positioning a proximal contact line specifying a periphery of the proposed dental bridge at an elevation above the bottom line but below an incisal surface of the proposed dental bridge in the CEREC program so that the proximal contact line defines a shape of a proximal area of the dental bridge that fits between the adjacent teeth bounding the volume while providing retainers that abut a surface of the adjacent teeth;
   shaping and positioning a labio-lingual line specifying a periphery of the proposed dental bridge at an elevation above the proximal contact line but below the incisal surface of the proposed dental bridge in the CEREC program so that the labio-lingual line defines a shape of a labio-lingual area of the dental bridge that fits between the adjacent teeth bounding the volume while providing retainers that abut a surface of the adjacent teeth; and
   shaping and positioning an incisal line specifying a periphery of the proposed dental bridge at the incisal surface in the CEREC program so that the incisal line defines a shape of the incisal surface that fits between the adjacent teeth bounding the volume.

2. The method of claim 1, further comprising:
   sending dental bridge data to a milling machine, the dental bridge data representing the proposed dental bridge produced by the CEREC program in accordance with the edited bottom line, edited proximal contact line, edited labio-lingual line, and the edited incisal line; and
   milling a blank at the milling machine according to the dental bridge data to produce a dental bridge from the data.

3. The method of claim 2, further comprising bonding the retainers of the dental bridge to the surface of the adjacent teeth to fill the volume with the bridge.

4. The method of claim 1, wherein shaping and positioning the bottom line, the proximal contact line, the labio-lingual line, and the incisal line are performed manually using editing tools of the CEREC program.

5. The method of claim 1, wherein shaping and positioning the bottom line, the proximal contact line, the labio-lingual line, and the incisal line are performed automatically using a programming patch to the CEREC program.

6. The method of claim 1, further comprising sending the image data from one computer that controls the image data to a receiving computer implementing the CEREC program and wherein the steps of shaping and positioning are performed on the receiving computer.

7. The method of claim 1, further comprising:
   editing a cant of the proposed bridge with a rotation tool of the CEREC program;
   editing a contour of a mesio-distal section of the proposed dental bridge; and
   editing a contour of a buccal-lingual section of the proposed dental bridge.

8. The method of claim 1, further comprising editing the contour of the retainers of the proposed dental bridge.

9. The method of claim 1, wherein at least one of the retainers is wing shaped.

10. A method of creating a dental bridge using a CEREC program, comprising:
    imaging a volume to fill with the dental bridge along with at least portions of adjacent teeth on both sides of the volume to produce image data regarding the volume to fill; and
    specifying a proposed dental bridge in the CEREC program in relation to the image data so that the proposed dental bridge fits between adjacent teeth and on or above a profile line bounding the volume, wherein the proposed dental bridge includes a pontic with integral retainers that abut a surface of the adjacent teeth.

11. The method of claim 10, further comprising:
    sending dental bridge data to a milling machine, the dental bridge data representing the proposed dental bridge produced by the CEREC program; and
    milling a blank at the milling machine according to the dental bridge data to produce a dental bridge from the data.

12. The method of claim 11, further comprising bonding the retainers of the dental bridge to the lingual surface of the adjacent teeth to fill the volume with the bridge.

13. The method of claim 10, wherein specifying a proposed dental bridge in the CEREC program in relation to the image data is performed manually using editing tools of the CEREC program.

14. The method of claim 10, wherein specifying a proposed dental bridge in the CEREC program in relation to the image data is performed automatically using a programming patch to the CEREC program.

15. The method of claim 10, further comprising sending the image data from one computer that creates the image data to a receiving computer implementing the CEREC program and wherein the step of specifying the proposed dental bridge is performed on the receiving computer.

16. The method of claim 10, wherein at least one of the retainers is wing shaped.

17. A computer system for creating a dental bridge using a CEREC program, comprising:

a memory for holding image data, the image data representing a volume to fill with the dental bridge and at least portions of adjacent teeth that bound the volume;

a processor configured to implement the CEREC program upon the image data, wherein the CEREC program is executed to:

shape and position a bottom line specifying a proposed dental bridge from the image data so that the bottom line defines a shape of the base of the dental bridge that fits between adjacent teeth bounding the volume, with the shape of the base including retainers that abut a surface of the adjacent teeth and with the bottom line elevation relative to a profile line from the image data so that the base of the dental bridge resides on or above the gum line and a surface of the adjacent teeth to be bonded;

shape and position a proximal contact line specifying a periphery of the proposed dental bridge at an elevation above the bottom line but below an incisal surface of the proposed dental bridge so that the proximal contact line defines a shape of a proximal area of the dental bridge that fits between the adjacent teeth bounding the volume while providing retainers that abut a surface of the adjacent teeth;

shape and position a labio-lingual line specifying a periphery of the proposed dental bridge at an elevation above the proximal contact line but below the incisal surface of the proposed dental bridge so that the labio-lingual line defines a shape of a labio-lingual area of the dental bridge that fits between the adjacent teeth bounding the volume while providing retainers that abut a surface of the adjacent teeth; and shape and position an incisal line specifying a periphery of the proposed dental bridge at the incisal surface so that the incisal line defines a shape of the incisal surface that fits between the adjacent teeth bounding the volume.

18. The computer system of claim 17, further comprising a milling system in communication with the processor, wherein the processor is configured to instruct the milling system to mill a blank into a dental bridge corresponding to the proposed dental bridge.

19. The computer system of claim 17, further comprising a display screen in communication with the processor, wherein the display screen shows the image of the volume and the adjacent teeth, the bottom line, the proximal contact line, the labio-lingual line, and the incisal line while being shaped and positioned.

20. The computer system of claim 17, wherein the processor is configured to execute CEREC to shape and position the bottom line, the proximal, the labio-lingual line, and the incisal line by receiving user input through a CEREC user interface.

21. The computer system of claim 17, wherein the processor is configured to execute CEREC and a program patch to automatically shape and position the bottom line, the proximal contact line, the labio-lingual line, and the incisal line.

22. The computer system of claim 17, wherein the CEREC program is further executed to:

edit a cant of the proposed bridge with a rotation tool;

edit a contour of a mesio-distal section of the proposed dental bridge;

edit a contour of a buccal-lingual section of the proposed dental bridge; and edit a contour of the retainers.

23. The computer system of claim 17, wherein at least one of the retainers is wing shaped.

24. A method of creating a dental bridge using a computer-aided design program utilizing a bottom line, a proximal contact line, a labio-lingual line, and an incisal line to specify a proposed dental bridge, comprising:

imaging a volume to fill with the dental bridge along with at least portions of adjacent teeth on both sides of the volume to produce image data regarding the volume to fill;

shaping and positioning a bottom line specifying a proposed dental bridge from the image data so that the bottom line defines a shape of the base of the proposed dental bridge that fits between adjacent teeth bounding the volume, with the shape of the base including retainers that abut a surface of the adjacent teeth and with the bottom line elevation specified relative to a profile line from the image data so that the base of the proposed dental bridge resides on or above the gum line and a surface of the adjacent teeth to be bonded;

shaping and positioning a proximal contact line specifying a periphery of the proposed dental bridge at an elevation above the bottom line but below an incisal surface of the proposed dental bridge so that the proximal contact line defines a shape of a proximal area of the dental bridge that fits between the adjacent teeth bounding the volume while providing retainers that extend over and abut a surface of the adjacent teeth;

shaping and positioning a labio-lingual line specifying a periphery of the proposed dental bridge at an elevation above the proximal contact line but below the incisal surface of the proposed dental bridge so that the labio-lingual line defines a shape of a labio-lingual area of the dental bridge that fits between the adjacent teeth bounding the volume while providing retainers that extend over and abut a surface of the adjacent teeth; and shaping and positioning an incisal line specifying a periphery of the proposed dental bridge at the incisal surface so that the incisal line defines a shape of the incisal surface that fits between the adjacent teeth bounding the volume.

25. The method of claim 24, further comprising:

editing a cant of the proposed bridge;

editing a contour of a mesio-distal section of the proposed dental bridge; and editing a contour of a buccal-lingual section of the proposed dental bridge.

26. The method of claim 24, further comprising editing the contour of the retainers of the proposed dental bridge.

27. The method of claim 24, wherein at least one of the retainers is wing shaped.

28. A method of creating a dental bridge using a computer-aided design program, comprising:

imaging a volume to fill with the dental bridge along with at least portions of adjacent teeth on both sides of the volume to produce image data regarding the volume to fill; and specifying a proposed dental bridge in relation to the image data so that the proposed dental bridge fits between adjacent teeth and on or above a profile line, wherein the proposed dental bridge includes a pontic with integral retainers that abut a surface of the adjacent teeth.

29. The method of claim 28, further comprising:

sending dental bridge data to a milling machine, the dental bridge data representing the proposed dental bridge; and milling a blank at the milling machine according to the dental bridge data to produce a dental bridge from the data.

30. The method of claim 29, further comprising bonding the retainers of the dental bridge to the lingual surface of the adjacent teeth to fill the volume with the bridge.

31. The method of claim 28, wherein at least one of the retainers is wing shaped.

* * * * *